United States Patent
Yamakita

(10) Patent No.: US 8,097,839 B2
(45) Date of Patent: Jan. 17, 2012

(54) RADIATION IMAGE PROCESSING APPARATUS FOR REMOVING PERIODIC PATTERNS CAUSED BY A SCATTERED RADIATION REMOVING MEANS

(75) Inventor: Hiroshi Yamakita, Ashigarakami-gun (JP)

(73) Assignee: Fujifilm Corporation, Tokyo (JP)

( * ) Notice: Subject to any disclaimer, the term of this patent is extended or adjusted under 35 U.S.C. 154(b) by 511 days.

(21) Appl. No.: 12/389,925

(22) Filed: Feb. 20, 2009

(65) Prior Publication Data
US 2009/0214130 A1    Aug. 27, 2009

(30) Foreign Application Priority Data
Feb. 22, 2008    (JP) .................................. 2008-040984

(51) Int. Cl.
*H01L 27/00*    (2006.01)
(52) U.S. Cl. ..................................... 250/208.1; 250/226

(58) Field of Classification Search ............... 250/208.1, 250/214 R, 226; 382/128–134, 260–265, 382/277–283, 298; 356/237.1
See application file for complete search history.

(56) References Cited

U.S. PATENT DOCUMENTS

| 6,075,840 | A | 6/2000 | Pellegrino et al. |
| 7,039,151 | B2 | 5/2006 | Tsujii |
| 7,826,682 | B2 * | 11/2010 | Behiels et al. ............... 382/275 |

FOREIGN PATENT DOCUMENTS
JP    2002-330344 A    11/2002

* cited by examiner

*Primary Examiner* — Que T Le
(74) *Attorney, Agent, or Firm* — Sughrue Mion, PLLC

(57) ABSTRACT

A filter processing means removes periodic patterns caused by a scattered radiation removing means from radiation images, which are obtained by detecting radiation that has passed through the scattered radiation removing means with a radiation detector. The filter processing means removes only the spatial frequency components of the periodic pattern from the radiation images.

5 Claims, 5 Drawing Sheets

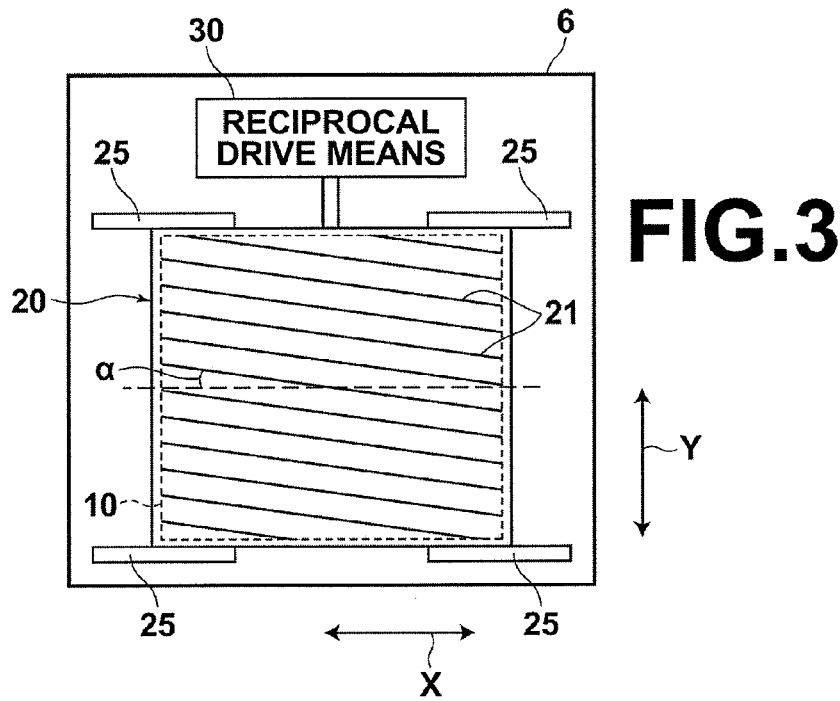
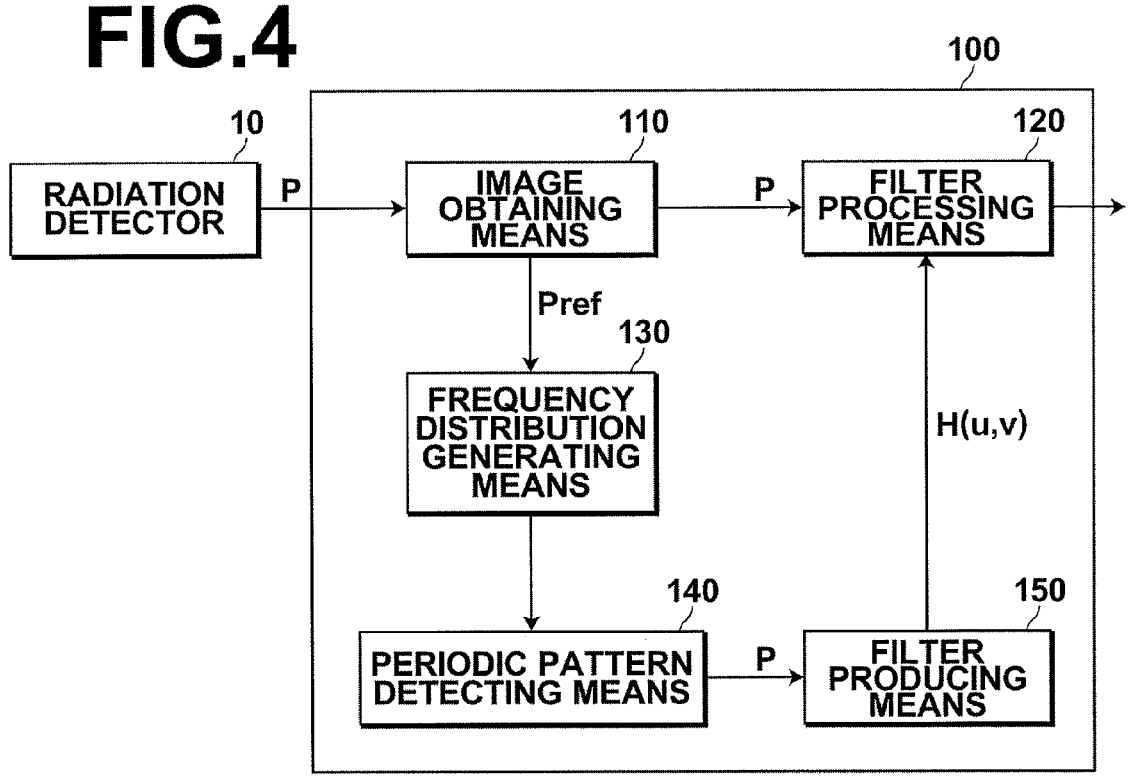

RADIATION IMAGE PROCESSING APPARATUS FOR REMOVING PERIODIC PATTERNS CAUSED BY A SCATTERED RADIATION REMOVING MEANS

BACKGROUND OF THE INVENTION

1. Field of the Invention

The present invention is related to a radiation image processing apparatus that removes periodic patterns from radiation images.

2. Description of the Related Art

Various types of radiation image detectors that generate charges by being irradiated with radiation which has passed through subjects and record radiation images of the subjects by accumulating the charges have been proposed and are in actual use in the field of medicine and the like. For example, there are radiation detectors that utilize amorphous selenium, which generates electrical charges when irradiated by radiation. In radiation image processing apparatuses, scattered radiation removing means (grids), constituted by a plurality of lead plates which are arranged parallel to each other, are provided between radiation sources that emit radiation and the radiation image detectors. This configuration enables scattered components of radiation to be removed by the scattered radiation removing means. When radiation images are obtained via the aforementioned scattered radiation removing means, periodic stripes are generated within the radiation images due to the scattered radiation removing means. Various proposals have been made to prevent deterioration of image quality due to the periodic stripes.

Japanese Unexamined Patent Publication No. 2002-330344 proposes deriving spatial frequency components of periodic patterns, which are determined by the lattice density of a scattered radiation removing means, then removing periodic patterns by administering a filtering process that removes frequency components having frequencies greater than or equal to the spatial frequency from radiation images. The invention disclosed in this document presumes that periodic patterns exist in the high frequency side, and that images of subjects are not present in frequency ranges greater than or equal to the spatial frequency of the scattered radiation removing means. U.S. Pat. No. 6,075,840 proposes to provide the plates of a scattered radiation removing means such that they are inclined at a predetermined angle with respect to a radiation detector. Further, U.S. Pat. No. 7,039,151 proposes to reciprocally move a scattered radiation removing means so as to prevent the generation of periodic stripes, which are caused by still scattered radiation removing means.

Recently, it is desired for lattice densities of scattered radiation removing means to be decreased, so as to improve the transmissivity of radiation. Here, in the case that the lattice density of the scattered radiation removing means of Japanese Unexamined Patent Publication No. 2002-330344 is decreased, the periodic patterns which are caused due to the scattered radiation removing means will be generated at the low frequency component side of the spatial frequency components. In addition, if the scattered radiation removing means is provided in an inclined manner or reciprocally moved as in U.S. Pat. Nos. 6,075,840 and 7,039,151, decreased lattice densities will not eliminate periodic patterns, but rather cause them to appear as low frequency components.

Meanwhile, image data that represent tissue structures are present as lower frequency components. In cases that the spatial frequency components of periodic patterns appear as low frequency components, there are cases that image components of subjects are present as higher frequency components than periodic patterns. Accordingly, there is a problem that frequency components that represent tissue structures will be removed as well, if all frequency components which are greater than or equal to the spatial frequency of the periodic pattern are removed, as in Japanese Unexamined Patent Publication No. 2002-330344.

Purposefully providing scattered radiation removing means at desired angles in order to avoid inclinations with respect to the main direction or a sub direction of a radiation detector and to prevent moiré patterns with the radiation detector from being generated, may be considered. These grids have angular components in addition to frequency components. Therefore, if these components are all removed, there is also a possibility that frequency components that represent tissue structures will be removed.

SUMMARY OF THE INVENTION

The present invention has been developed in view of the foregoing circumstances. It is an object of the present invention to provide a radiation image processing apparatus which is capable of removing only periodic patterns caused by scattered radiation removing means from within radiation images, without removing images of subjects.

A radiation image processing apparatus of the present invention is equipped with a scattered radiation removing means, for removing scattered components of radiation which has passed through a subject, and removes periodic patterns caused by the scattered radiation removing means from radiation images, which are obtained by detecting the radiation that has passed through the scattered radiation removing means with a radiation detector, and is characterized by comprising:

filter processing means, for removing only the spatial frequency components of the periodic pattern from the radiation images.

Here, the "radiation images" refer to all images which are obtained by detecting radiation which has been irradiated onto subjects. Examples of such images include: radiation images obtained by a mammography apparatus; and radiation images obtained by imaging the chests of subjects. The "radiation images" are not limited to those for medical use, and may also include radiation images which are employed for non destructive inspections.

The pattern of the scattered radiation removing means is not limited, as long as it is capable of removing scattered components of radiation. The scattered radiation removing means may be constituted by a plurality of plates which are provided along the main direction or the sub direction of the radiation detector. Alternatively, the scattered radiation removing means may be constituted by a plurality of plates which are provided such that they are inclined with respect to the main direction of the sub direction of the radiation detector. Further, the scattered radiation removing means may be configured to be static with respect to the radiation detector, or configured to move reciprocally with respect to the radiation detector.

The radiation image processing apparatus of the present invention may further comprise:

frequency distribution generating means, for generating a two dimensional frequency distribution of a reference image, which is detected when imaging is performed by the radiation detector without a subject, by performing frequency analysis of the reference image;

periodic pattern detecting means, for detecting the spatial frequency components of the periodic pattern, based on peaks which are present within the two dimensional frequency distribution generated by the frequency distribution generating means; and filter producing means, for producing a filter that removes only the spatial frequency components detected by the periodic pattern detecting means from the radiation image.

In this case, the periodic pattern detecting means may detect the full widths at half maximum of the peaks of the two dimensional frequency distribution as the spatial frequency components of the periodic pattern.

The radiation image processing apparatus of the present invention removes periodic patterns caused by the scattered radiation removing means from radiation images, which are obtained by detecting the radiation that has passed through the scattered radiation removing means with a radiation detector, and is characterized by comprising the filter processing means, for removing only the spatial frequency components of the periodic pattern from the radiation images. Therefore, removal of images of subjects having components greater than or equal to the frequency components of the periodic pattern can be minimized.

Note that the radiation image processing apparatus of the present invention may further comprise: the frequency distribution generating means, for generating a two dimensional frequency distribution of a reference image, which is detected when imaging is performed by the radiation detector without a subject, by performing frequency analysis of the reference image; the periodic pattern detecting means, for detecting the spatial frequency components of the periodic pattern, based on peaks which are present within the two dimensional frequency distribution generated by the frequency distribution generating means; and the filter producing means, for producing a filter that removes only the spatial frequency components detected by the periodic pattern detecting means from the radiation image. In this case, the reference image, which actually detected by the radiation detector, can be employed to detect the spatial frequency components of the periodic pattern to produce the filter. Therefore, the periodic pattern can be removed accurately.

Further, the periodic pattern detecting means may detect the full widths at half maximum of the peaks of the two dimensional frequency distribution as the spatial frequency components of the periodic pattern. In this case, the periodic pattern can be positively removed, while minimizing removal of components of images of subjects having frequencies greater than or equal to those of the frequency components of the periodic pattern.

The scattered radiation removing means may be constituted by a plurality of plates which are provided such that they are inclined with respect to the main direction or the sub direction of the radiation detector. Alternatively, the scattered radiation removing means may be configured to move reciprocally with respect to the radiation detector. In both these cases, the periodic patterns caused by the scattered radiation removing means appear as predetermined frequency components. By producing filters that remove only these frequency components and performing the filtering process, the periodic patterns can be positively removed, while minimizing removal of components of images of subjects having frequencies greater than or equal to those of the frequency components of the periodic pattern.

BRIEF DESCRIPTION OF THE DRAWINGS

FIG. 3 is a plan view of that illustrates the inner structure of the imaging stage of the radiation image detecting apparatus illustrated in FIG. 1.

FIG. 4 is a block diagram that illustrates the radiation image processing apparatus according to a preferred embodiment of the present invention.

BEST MODE FOR CARRYING OUT THE INVENTION

Figure 1:
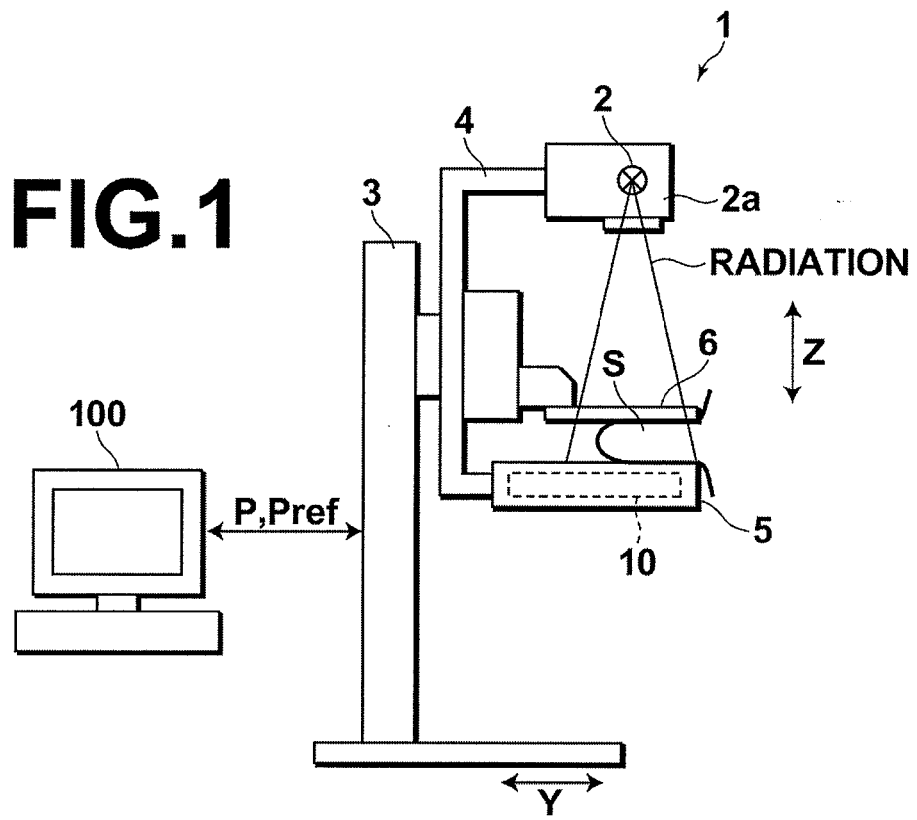
FIG. 1 is a diagram that schematically illustrates a radiation image detecting apparatus, according to a preferred embodiment of the present invention.

Hereinafter, a radiation image processing apparatus of the present invention will be described with reference to the attached drawings. FIG. 1 is a diagram that schematically illustrates a radiation image detecting apparatus 1 for obtaining radiation images, according to a preferred embodiment of the present invention. The radiation image detecting apparatus 1 of FIG. 1 is a mammography apparatus for obtaining radiation images of breasts, is equipped with: a radiation source 2; a base 3; a support 4; an imaging stage 5; and a pressing plate 6. The base 3 holds the support 4 such that the support 4 is movable in the direction indicated by arrow Z, according to the position of subjects S. The radiation source 2 emits radiation toward the subjects S, and is housed in a radiation source housing section 2a, which is mounted to the upper portion of the support 4.

The imaging stage 5 houses a radiation detector 10 therein. The radiation detector 10 obtains radiation image Ps by detecting radiation which is emitted from the radiation source 2 and has passed through the subjects S. The imaging stage 5 is mounted to the lower portion of the support 4 so as to face the radiation source 2. In addition, the pressing plate 6 for pressing the subject S against the imaging stage 5 is provided above the imaging stage 5. The pressing plate 6 is mounted such that it is movable in the direction indicated by arrow Z with respect to the support 4.

The radiation detector 10 accumulates radiation image data constituted by radiation which has passed through the subjects S as electrostatic latent images. The accumulated electrostatic latent images are read out, to detect the transmittance distribution of the radiation as the radiation images. Note that the radiation detector 10 may be of any configuration as long as it detects radiation and outputs the detected radiation as image data. Examples of radiation detectors that may be employed as the radiation detector 10 include TFT type solid state detectors and optical readout type solid state detectors.

Figure 2:
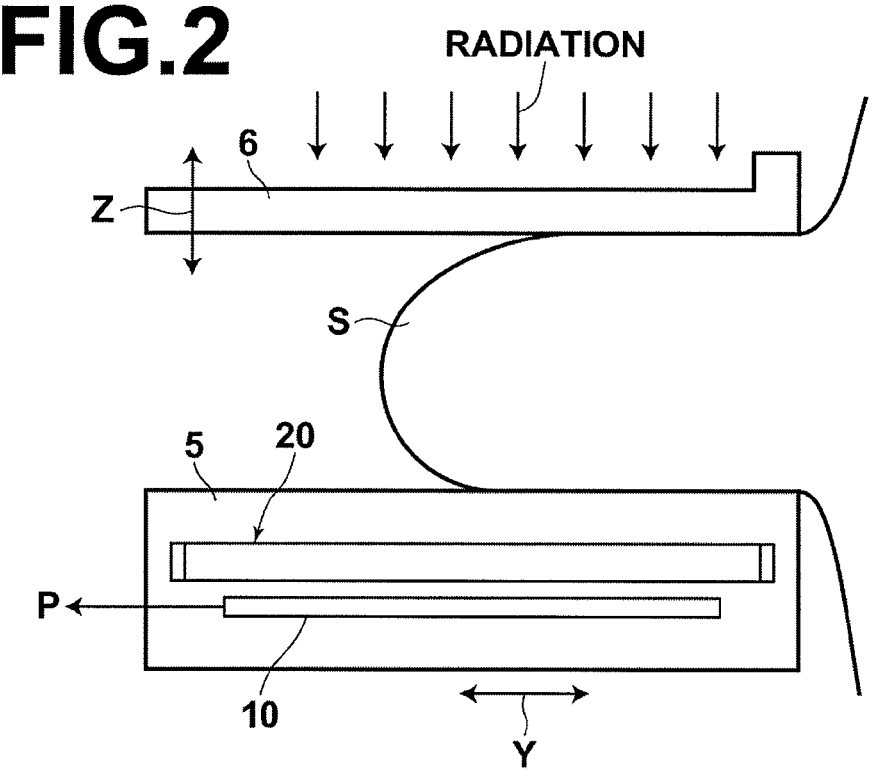
FIG. 2 is a schematic diagram that illustrates the inner structure of an imaging stage of the radiation image detecting apparatus illustrated in FIG. 1.

FIG. 2 is a schematic diagram that illustrates the inner structure of the imaging stage 5 of FIG. 1. FIG. 3 is a plan view of the imaging stage 5. A scattered radiation removing means 20 is provided within the imaging stage 5 such that it is positioned between the radiation source 2 and the radiation detector 10. The scattered radiation removing means 20 transmits non scattered components of radiation and absorbs (removes) scattered radiation components with plates 21. The scattered radiation removing means 20 is of a configuration in which a plurality of plates 21 made of lead or the like are arranged parallel to each other at predetermined intervals (approximately 0.3 mm, for example) such that they point toward the radiation source (focal point. Here, the plates 21 of the scattered radiation removing means 20 are provided such that the longitudinal directions thereof are inclined at an angle α with respect to the main direction of the radiation detector 10 (indicated by arrow X).

A reciprocal driving means 30 that moves the scattered radiation removing means 20 reciprocally with respect to the radiation detector 10 is attached to the scattered radiation removing means 20. The reciprocal driving means 30 is constituted by a mechanism that converts the rotation of a motor into reciprocal motion, for example. The reciprocal driving means 30 moves the scattered radiation removing means 20 reciprocally in a direction perpendicular to the longitudinal direction of the plates 21 of the scattered radiation removing means 20 (indicated by arrow Y) at a constant speed.

A radiation image processing apparatus 100 that administers various image processes onto the radiation images P obtained by the radiation detector 10 and displays the radiation images P is connected to the radiation image detecting apparatus of FIG. 1. FIG. 4 is a block diagram that illustrates the radiation image processing apparatus 100 according to a preferred embodiment of the present invention. The radiation image processing apparatus 100 illustrated in FIG. 4 is equipped with: an image obtaining means 110; and a filter processing means 120. The image obtaining means 110 obtains radiation images P0, which are obtained by the radiation detector 10, as digital data.

The filter processing means 120 administers a filtering process that removes only the spatial frequency components of a periodic pattern onto the radiation images P obtained by the image obtaining means 110. The filter processing means 120 generates Fourier transformed images $F(u, v)$ by administering Fourier transform on the radiation images. Thereafter, the filter processing means 120 integrates the Fourier transformed images $F(u, v)$ with a filter $H(u, v)$, to derive filtered Fourier transformed images $F'(u, v)$ of the radiation images P. Finally, the filter processing means 120 administers reverse Fourier transform on the filtered Fourier transformed images $F'(u, v)$, to obtain filtered radiation images P.

Here, the radiation image processing apparatus 100 is equipped with a data holding means that has a filter $H(u, v)$ that removes only the spatial frequency components of the periodic pattern. The data holding means may have a filter $H(u, v)$ which is produced in advance. Alternatively, the radiation image processing apparatus may have a function of producing a filter $H(u, v)$ to be employed in the filtering process from a reference image Pref. In this case, the data holding means is equipped with: a frequency distribution generating means 130; a periodic pattern detecting means 140; and a filter producing means 150.

Figure 5:
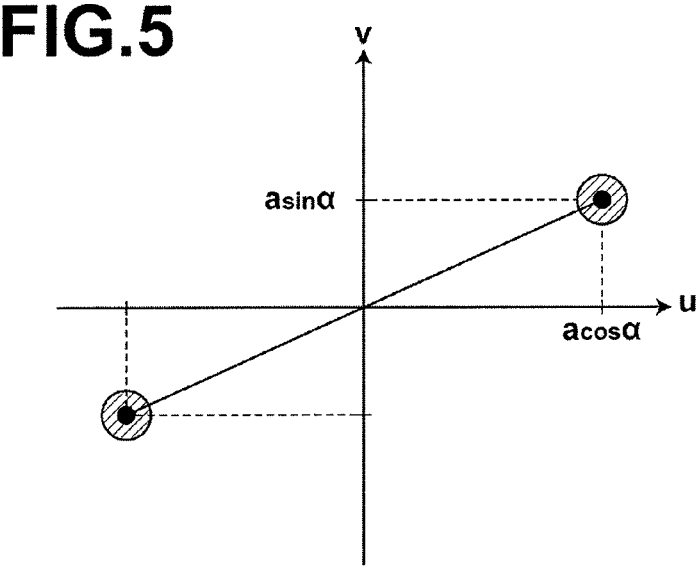
FIG. 5 is a graph that illustrates an example of a periodic pattern which is derived when frequency analysis is administered on a reference image by the radiation image processing apparatus of FIG. 4.
Figure 6:
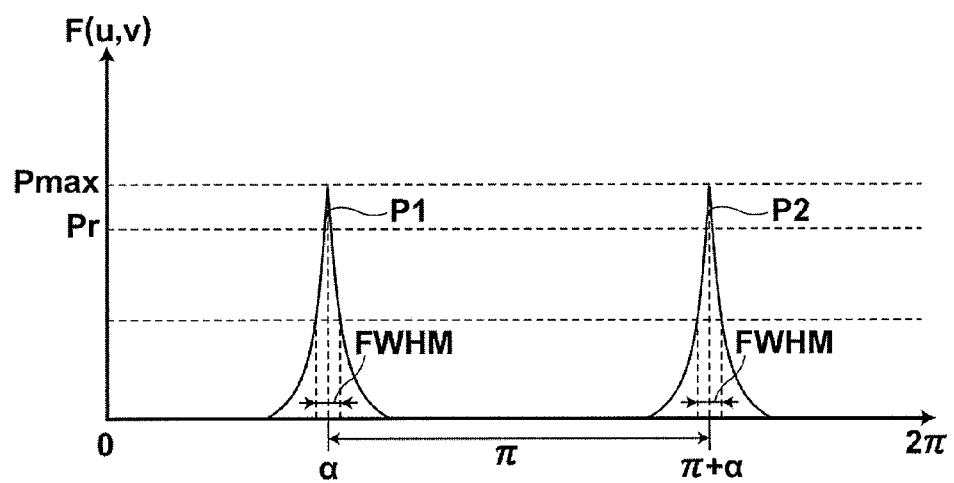
FIG. 6 is a graph that illustrates an example of a periodic pattern which is derived when frequency analysis is administered on a reference image by the radiation image processing apparatus of FIG. 4.

The frequency distribution generating means 130 generates a two dimensional frequency distribution of the reference image Pref, which is detected when imaging is performed by the radiation detector 10 without a subject, by performing frequency analysis of the reference image Pref. Specifically, the frequency distribution generating means 130 generates a frequency distribution by administering a two dimensional Fourier space onto the reference image Pref. Then, spatial frequency components of a periodic pattern appear at positions which are inclined at an angle α from the u axis, as illustrated in FIG. 5. Here, if the lattice density of the scattered radiation removing means is a(c/mm), u is designated as u=acos θ, v is designated as v=asin θ along a circumference $a=(u^2+v^2)^{1/2}$ of FIG. 5, and the angle θ is designated as a variable, a two dimensional frequency distribution is generated having two peaks p1 and p2 as illustrated in FIG. 6 is generated.

The periodic pattern detecting means 140 of FIG. 4, detects the spatial frequency components of the periodic pattern caused by the scattered radiation removing means 20, based on the peaks p1 and p2, which are present within the two dimensional frequency distribution generated by the frequency distribution generating means 130. Specifically, the periodic pattern detecting means 140 detects components p1 and p2 which are grater than a predetermined threshold value Pr, from within the two dimensional frequency distribution of FIG. 6. Thereafter, the periodic pattern detecting means 140 detects the full widths at half maximum of the detected peaks p1 and p2, based on the peak values Pmax thereof, as the spatial frequency components of the periodic pattern.

Figure 7A:
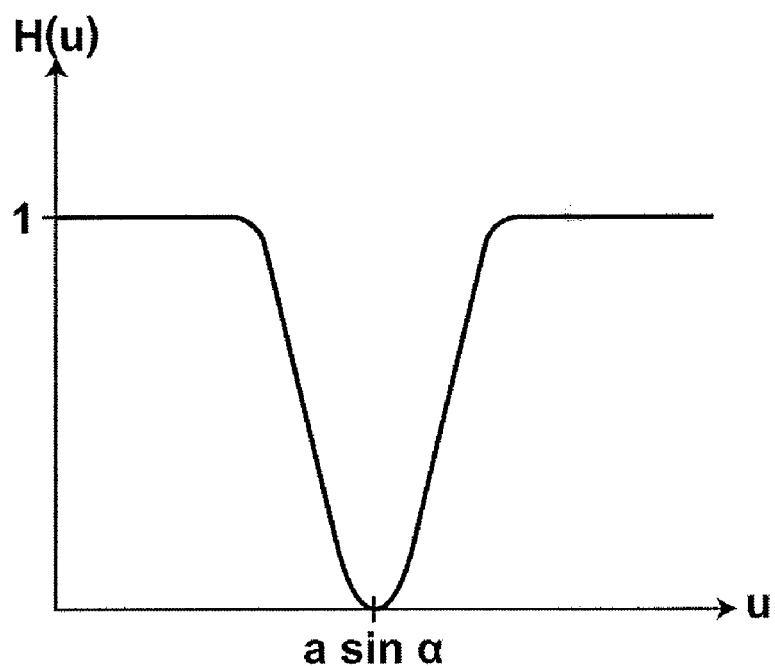
FIG. 7A and FIG. 7B are graphs that illustrate an example of a filter which is produced by a filter producing means of FIG. 4.
Figure 7B:
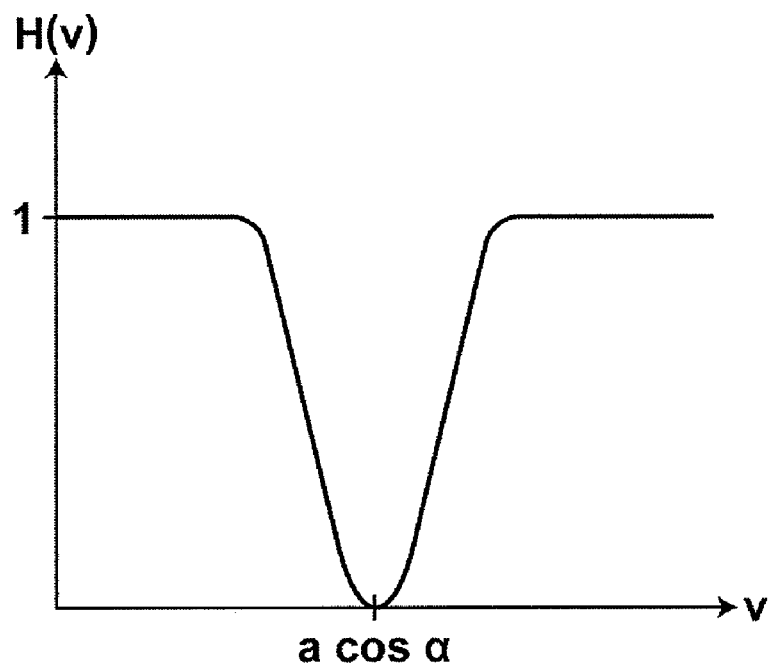

The filter producing means 150 of FIG. 4 produces a filter $H(u, v)$ that removes only the spatial frequency components detected by the periodic pattern detecting means 140. At this time, the filter producing means 150 produces the filter $H(u, v)$ with respect to the u direction and the v direction of the Fourier transformed image, as illustrated in FIGS. 7A and 7B. The filter processing means 120 applies the filter $H(u, v)$ illustrated in FIGS. 7A and 7B, to administer the aforementioned filtering process.

By removing only the spatial frequency components of the periodic pattern from the radiation images, removal of images of subjects by the filtering process can be minimized. That is, in the case that a conventional filtering process that removes all frequency components having frequencies greater than or equal to the frequency components of the periodic pattern, there is a possibility that images of subjects that include low frequency components, may also be removed.

Meanwhile, purposefully providing the scattered radiation removing means 20 in the radiation image detecting apparatus 1 at desired angles as illustrated in FIG. 3 in order to avoid inclinations with respect to the main direction or a sub direction of a radiation detector 10 and to prevent moiré patterns with the radiation detector 10 from being generated, may be considered. In cases that the scattered radiation removing means 20, which is inclined in this manner, is reciprocally moved with respect to the radiation detector 10, the spatial frequency components of the periodic pattern within a Fourier space are lower signals (this does not mean that the frequency of the spatial frequency components are low) than those of a static scattered radiation removing means 20. However, in either case, the spatial frequency components will be of a predetermined frequency, which is determined by the lattice density of the scattered radiation removing means 20 (which is unrelated to the spatial frequency). By the filter processing means 120 administering the filtering process that takes advantage of this fact and removing only the spatial frequency components of the periodic pattern, removal of images of subjects by the filtering process can be minimized.

The radiation image processing apparatus of the embodiment described above removes periodic patterns caused by the scattered radiation removing means 20 from radiation images P, which are obtained by detecting the radiation that has passed through the scattered radiation removing means 20 with a radiation detector 10, and is characterized by comprising the filter processing means 120, for removing only the spatial frequency components of the periodic pattern from the radiation images P. Therefore, removal of images of subjects having components greater than or equal to the frequency components of the periodic pattern can be minimized.

As illustrated in FIG. 4, the radiation image processing apparatus of the embodiment described above comprises: the frequency distribution generating means 130, for generating a two dimensional frequency distribution of a reference image Pref, which is detected when imaging is performed by the radiation detector 10 without a subject, by performing frequency analysis of the reference image Pref; the periodic pattern detecting means 140, for detecting the spatial frequency components of the periodic pattern, based on the peaks p1 and p2 which are present within the two dimensional frequency distribution generated by the frequency distribution generating means 130; and the filter producing means 150, for producing a filter that removes only the spatial frequency components detected by the periodic pattern detecting means 140 from the radiation images P. Therefore, the reference image Pref, which actually detected by the radiation detector 10, can be employed to detect the spatial frequency components of the periodic pattern to produce the filter H(u, v). Accordingly, the periodic pattern can be removed accurately.

Further, the periodic pattern detecting means 140 detects the full widths at half maximum of the peaks p1 and p2 of the two dimensional frequency distribution as the spatial frequency components of the periodic pattern, as illustrated in FIG. 6. Therefore, the periodic pattern can be positively removed, while minimizing removal of components of images of subjects having frequencies greater than or equal to those of the frequency components of the periodic pattern.

The scattered radiation removing means 20 is constituted by the plurality of plates 21 which are provided such that they are inclined with respect to the main direction (indicated by arrow X) and the sub direction (indicated by arrow Y) of the radiation detector 10, as illustrated in FIG. 3. In addition, the scattered radiation removing means 20 is configured to move reciprocally with respect to the radiation detector 10. In this configuration as well, the periodic patterns caused by the scattered radiation removing means 20 appear as predetermined frequency components. By producing the filter that removes only these frequency components and performing the filtering process, the periodic patterns can be positively removed, while minimizing removal of components of images of subjects having frequencies greater than or equal to those of the frequency components of the periodic pattern.

Figure 8A:
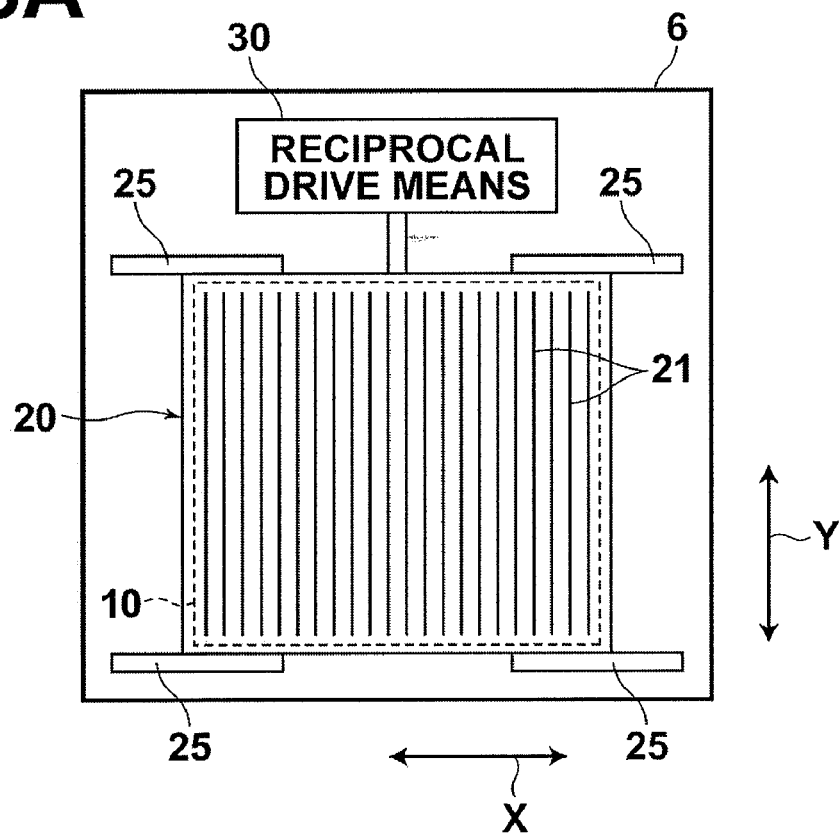
FIG. 8A and FIG. 8B illustrate an alternate embodiment of the scattered radiation removing means, and the spatial frequency components thereof.
Figure 8B:
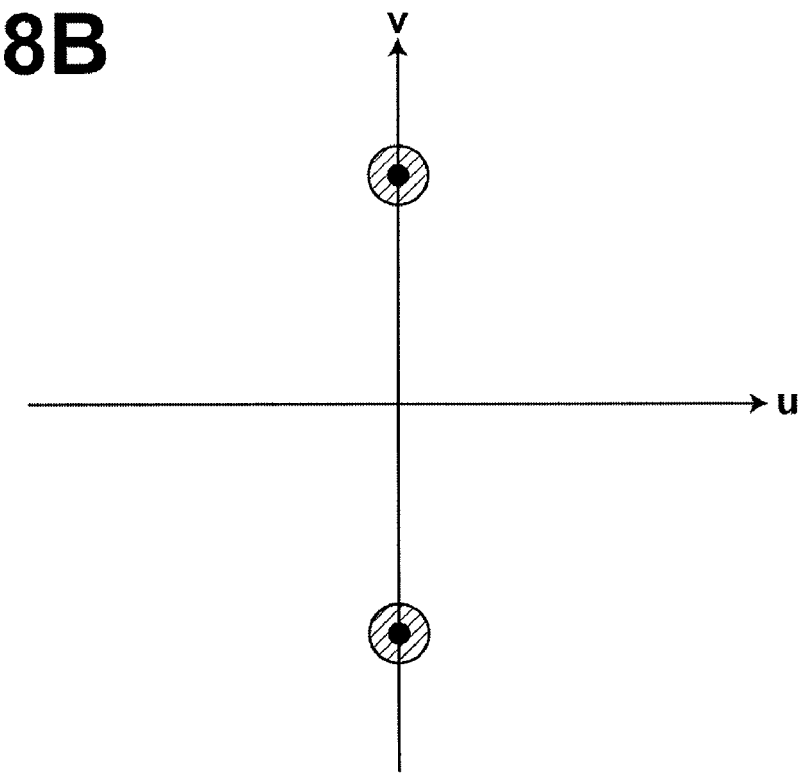

The present invention is not limited to the embodiment described above. For example, FIG. 3 illustrates a case in which the scattered radiation removing means 20 is inclined with respect to both the main direction and the sub direction of the radiation detector 10. However, a configuration may be adopted, wherein the longitudinal directions of the plates 21 extend along the sub direction (or the main direction) of the radiation detector 10, as illustrated in FIG. 8A. At this time, the frequency components of the periodic pattern within a Fourier space F(u, v) appear on the v axis (or the u axis) as illustrated in FIG. 8B. In this case, the filter producing means 150 produces a filter that removes only the aforementioned frequency components, and the filter processing means 120 administers the filtering process employing the filter which is produced by the filter producing means 150.

FIG. 3 illustrates an example in which the scattered radiation removing means 20 is moved reciprocally. However, the filtering process of the present invention may be applied in cases in which the scattered radiation removing means 20 is static. That is, even in cases that the scattered radiation removing means 20 is static, the periodic pattern appears as low frequency components as the lattice density thereof decreases. Therefore, the filtering process of the present invention is effective.

What is claimed is:

1. A radiation image processing apparatus equipped with a scattered radiation removing means for removing scattered components of radiation, that removes periodic patterns caused by the scattered radiation removing means from radiation images, which are obtained by detecting radiation, which has passed through a subject, with a radiation detector via the scattered radiation removing means, comprising:

data holding means, for holding spatial frequency components of the periodic patterns within the radiation images; and filter processing means, for removing only the spatial frequency components of the periodic pattern, which are held in the data holding means, from the radiation images.

2. A radiation image processing apparatus as defined in claim 1, wherein the data holding means comprises:

frequency distribution generating means, for generating a two dimensional frequency distribution of a reference image, which is detected by performing imaging by the radiation detector in a state without a subject, by performing frequency analysis of the reference image;

periodic pattern detecting means, for detecting the spatial frequency components of the periodic pattern, based on peaks which are present within the two dimensional frequency distribution generated by the frequency distribution generating means; and filter producing means, for producing a filter that removes only the spatial frequency components detected by the periodic pattern detecting means from the radiation image.

3. A radiation image processing apparatus as defined in claim 2, wherein:

the periodic pattern detecting means detects the full widths at half maximum of the peaks of the two dimensional frequency distribution as the spatial frequency components of the periodic pattern.

4. A radiation image processing apparatus as defined in claim 1, wherein:

the scattered radiation removing means is equipped with a plurality of plates, which are provided such that they are inclined with respect to a main direction and a sub direction of the radiation detector.

5. A radiation image processing apparatus as defined in claim 1, wherein:

the scattered radiation removing means moves reciprocally with respect to the radiation detector.

* * * * *